United States Patent [19]
Sakakibara et al.

[11] Patent Number: 5,767,237
[45] Date of Patent: Jun. 16, 1998

[54] PEPTIDE DERIVATIVES

[75] Inventors: Kyoichi Sakakibara, Tokyo; Masaaki Gondo, Yokohama; Koichi Miyazaki, Ebina; Takeshi Ito, Kawasaki; Akihiro Sugimura, Kawasaki; Motohiro Kobayashi, Kawasaki, all of Japan

[73] Assignee: Teikoku Hormone Mfg. Co., Ltd., Tokyo, Japan

[21] Appl. No.: 619,606

[22] PCT Filed: Sep. 22, 1994

[86] PCT No.: PCT/JP94/01560

§ 371 Date: Apr. 1, 1996

§ 102(e) Date: Apr. 1, 1996

[87] PCT Pub. No.: WO95/09864

PCT Pub. Date: Apr. 13, 1995

[30] Foreign Application Priority Data

Oct. 1, 1993 [JP] Japan .................. 5-269642

[51] Int. Cl.$^6$ .............. A61K 38/00; C07K 5/00; C07K 7/00; C07K 17/00
[52] U.S. Cl. ................... 530/330; 514/17
[58] Field of Search ................ 530/330

[56] References Cited

U.S. PATENT DOCUMENTS

| | | | |
|---|---|---|---|
| 4,816,444 | 3/1989 | Pettit et al. | 514/17 |
| 4,978,744 | 12/1990 | Pettit et al. | 530/330 |
| 5,410,024 | 4/1995 | Pettit et al. | 530/330 |
| 5,635,483 | 6/1997 | Pettit et al. | 514/17 |

FOREIGN PATENT DOCUMENTS

| | | |
|---|---|---|
| 0 600 744 | 6/1994 | European Pat. Off. |
| 0 612 762 | 8/1994 | European Pat. Off. |

OTHER PUBLICATIONS

Pettit et al., The Isolation and Structure of a Remarkable Marine Animal Antineoplastic Constituent: Dolastatin 10$^{1a}$, J. Am. Chem. Soc., 1987, 109, 6883–6885.

*Primary Examiner*—Cecilia J. Tsang
*Assistant Examiner*—Michael Borin
*Attorney, Agent, or Firm*—Wenderoth, Lind & Ponack, LLP

[57] ABSTRACT

A peptide derivative represented by the following formula or a salt thereof

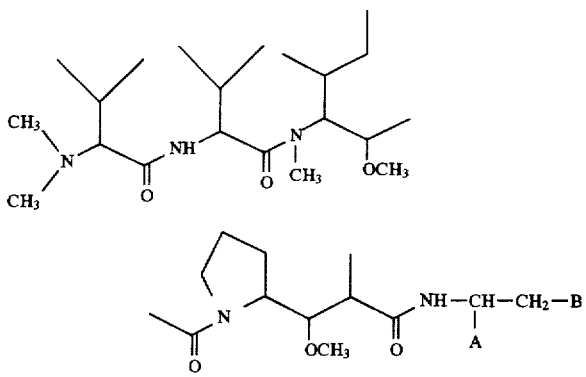

wherein A and B each represent either of the following (a) and (b), (a) A represents a hydrogen atom, and B represents a phenyl group substituted with a halogen atom, hydroxyl group, lower alkyl group or lower alkoxy group, or a heteroaryl group, (b) A represents —CONH—$R^1$, —CSNH—$R^1$, a hydroxymethyl group, a lower alkoxycarbonyl group or a carboxyl group, wherein $R^1$ represents a lower alkyl group or a heteroaryl group, and B represents a phenyl group optionally substituted with a halogen atom, hydroxyl group, lower alkyl group or lower alkoxy group, has an antitumor activity stronger than that of dolastatin 10, and is useful as an anticancer or antitumor agent.

2 Claims, No Drawings

PEPTIDE DERIVATIVES

TECHNICAL FIELD

This invention relates to a novel peptide derivative having an antitumor activity, and, more detailedly, relates to a peptide derivative represented by the following formula or a salt thereof

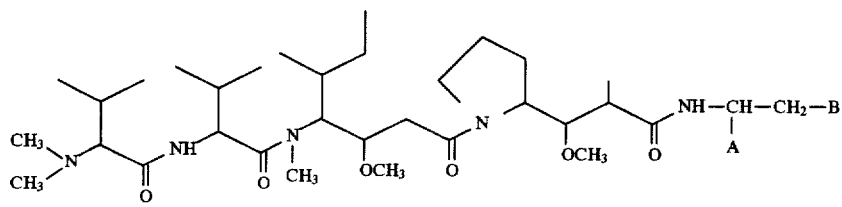

(I)

wherein A and B each represent either of the following (a) and (b), (a) A represents a hydrogen atom, and B represents a phenyl group substituted with a halogen atom, hydroxyl group, lower alkyl group or lower alkoxy group, or a heteroaryl group, (b) A represents —CONH—$R^1$, —CSNH—$R^1$, a hydroxymethyl group, a lower alkoxycarbonyl group or a carboxyl group, wherein, $R^1$ represents a lower alkyl group or a heteroaryl group, and B represents a phenyl group optionally substituted with a halogen atom, hydroxyl group, lower alkyl group or lower alkoxy group.

BACKGROUND ART

Peptides having a cytostatic activity and/or an antineoplasm activity have been isolated from marine molluscs, sea hare *Dolabella auricularia* and these peptides are called dolastatins 1 to 15. Among them, dolastatin 10 is a pentapeptide extracted from *Dolabella auricularia* from the Indian Ocean in 1987 by G. R. Pettit, et al. and having the following structural formula, and is said to be the strongest cytostatic substance presently known (see, G. R. Pettit, et al., J. Am. Chem. Soc., 109, 6883 (1987) and U.S. Pat. No. 4,816,444).

DISCLOSURE OF INVENTION

In the present description, the term "lower" means that the number of the carbon atoms of a group or compound to which this term is attached is 6 or less, preferably 4 or less.

In the above formula (I), as the "lower alkyl group", there can, for example, be mentioned methyl, ethyl, n-propyl, isopropyl, n-butyl, isobutyl, sec-butyl, tert-butyl, n-hexyl groups, etc. and as the "lower alkoxy group", there can, for example, be mentioned methoxy, ethoxy, n-propoxy, isopropoxy, n-butoxy groups, etc. Further, the "halogen atom" includes fluorine, chlorine, bromine and iodine atoms.

The "heteroaryl group" means an aromatic heterocyclic group containing hetero atom(s) selected from O, S and N, preferably, 5 or 6-membered heterocyclic group containing 1 to 4 hetero atoms, such as thienyl, furyl, pyrrolyl, imidazolyl, thiazolyl, oxazolyl, thiadiazolyl, tetrazolyl, pyridyl, pyrimidinyl, triazinyl groups, etc.

The "phenyl group substituted with a halogen atom, hydroxyl group, lower alkyl group or lower alkoxy group" represented by the symbol B includes a phenyl group substituted with one halogen atom, hydroxyl group, lower alkyl group or lower alkoxy group, and there can, for example, be mentioned 2-fluorophenyl, 2-chloro-phenyl, 2-bromophenyl, 3-fluorophenyl, 3-iodophenyl, 4-chlorophenyl, 4-bromophenyl, 2-hydroxyphenyl, 2-methylphenyl, 4-ethylphenyl, 2-methoxyphenyl, 4-ethoxyphenyl groups, etc. Further, the "phenyl group optionally substituted with a halogen atom, hydroxyl group, lower alkyl group or lower alkoxy group" includes an unsubstituted phenyl group besides the above substituted phenyl groups.

A group of preferred compounds in the invention are compounds of the above formula (I) wherein A represents a

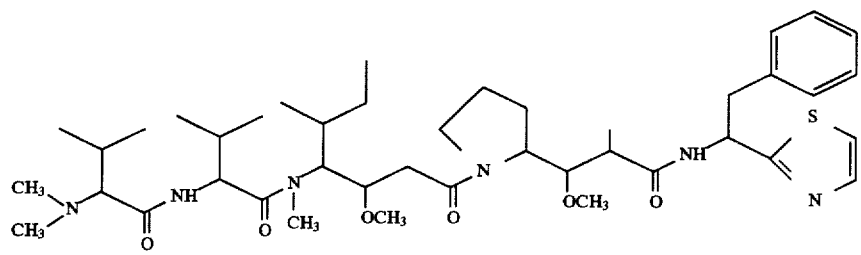

[Dolastatin 10]

Further, recently, publication was made on the total synthesis of dolastatin 10 itself (see, U.S. Pat. No. 4,978,744).

In this connection, the present inventors previously disclosed certain dolastatin 10 derivatives (see, WO93/03054 Pamphlet).

The present inventors found that certain dolastatin 10 derivatives wherein the dolaphenine (which means an α-(thiazolyl)phenethylamino group) at the C-terminus of dolastatin 10 is substituted with another substituent have a much stronger antitumor activity than that of dolastatin 10.

hydrogen atom and B represents a phenyl group substituted with a halogen atom, hydroxyl group, lower alkyl group or lower alkoxy group, or a heteroaryl group, particularly compounds of the above formula (I) wherein B represents a phenyl group substituted with a halogen atom, hydroxyl group, lower alkyl group or lower alkoxy group; a thienyl group; or a pyridyl group.

Another group of preferred compounds are compounds of the above formula (I) wherein A represents —CONH—$R^1$, —CSNH—$R^1$, a hydroxymethyl group, a lower alkoxycarbonyl group or a carboxyl group, wherein $R^1$ represents a lower alkyl group or a heteroaryl group, and B represents a phenyl group optionally substituted with a halogen atom, hydroxyl group, lower alkyl group or lower alkoxy group, particularly compounds of the above formula (I) wherein A represents —CONH—R¹, —CSNH—R¹, a hydroxymethyl group, a lower alkoxycarbonyl group or a carboxyl group, wherein R¹ represents a lower alkyl group, a thiazolyl group or thiadiazolyl group, and B represents an unsubstituted phenyl group.

In the compounds of the above formula (I) of the invention, the carbon atoms to which an isopropyl group, a sec-butyl group, a methoxy group and a methyl group bind respectively are asymmetric carbon atoms, and therefore, they can arbitrary have an R- or S-configuration. All those compounds are included in the scope of the invention, but in view of pharmacological activity, compounds having the same configuration as dolastatin 10 are preferred.

The peptide compounds of the above formula (I) can, further, exist as salts, and as examples of such salts, there can be mentioned hydrochlorides, hydrobromides, trifluoroacetates, p-toluenesulfonates, acetates, etc.

According to the invention, a peptide compound of the above formula (I) can be prepared by condensing the respective amino acids or peptide fragments, for example, according to a liquid phase synthesis method (see, E. Schröder and K. Lübke, "The Peptides", volume 1, pages 76–136, 1965, published by Academic Press) known in the field of peptide chemistry.

For example, for avoiding racemization at the condensation reaction, it is preferred to conduct synthesis by condensing a tripeptide fragment of the following formula (II)

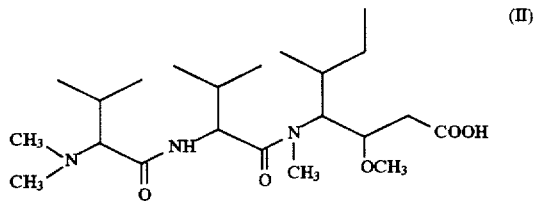

with a fragment of the following formula (III)

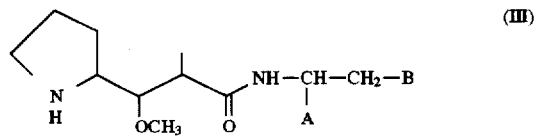

wherein A and B are as defined above.

Further, for synthesizing many compounds of the invention efficiently, it is preferred to conduct the synthesis by condensing a tetrapeptide fragment of the following formula (IV)

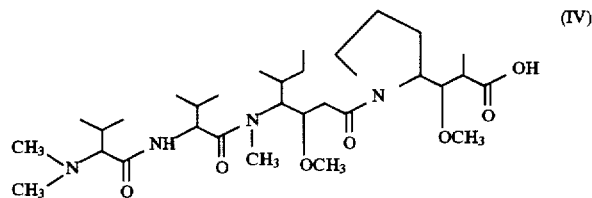

with a fragment of the following formula (V)

wherein A and B are as defined above.

The condensation reaction can be conducted, generally, by treating the fragments with a condensing agent, e.g. dicyclohexylcarbodiimide (DCC), diphenyl phosphoryl azide (DPPA) or diethyl phosphorocyanidate (DEPC), a so-called BOP reagent, or the like in an inert solvent such as, for example, chloroform, ethyl acetate, tetrahydrofuran (THF), dimethylformamide (DMF) or acetonitrile, if necessary in the presence of an organic base such as, for example, triethylamine, N-methylmorpholine or diisopropylethylamine (DIEA).

The reaction temperature is usually −10° C. to room temperature, preferably around 0° C. The ratios of the compound of the formula (III), the organic base and the condensing agent to the compound of the formula (II) are not strictly limited, but, usually, it is advantageous to use the compound of the formula (III) of at least one mole, preferably of the order of 1.0 to 1.1 moles, the organic base of the order of 2 moles, and the condensing agent of the equimolar order, respectively per mole of the compound of the formula (II).

A compound of the formula (I) wherein A represents a carboxyl group can also be prepared by alkali hydrolysis of the compound of the formula (I) wherein A represents a lower alkoxycarbonyl group.

The isolation and purification of thus obtained peptide compound of the formula (I) from the reaction mixture can be conducted by methods known per se, for example by recrystallization, ion exchange chromatography, gel filtration, high performance liquid chromatography, etc.

The compounds of the above formula (III) and (IV) used as starting materials in the above reaction are novel compounds not disclosed in prior literatures, and can easily be prepared by condensing amino acids, which are constituents thereof, according to a liquid phase synthesis method.

The peptide compounds of the formula (I) of the invention have a higher antitumor activity than dolastatin 10, and have a large therapeutic index, and are useful for treatment of acute myelocytic leukemia, acute lymphocytic leukemia, chronic melanoma, pulmonary adenocarcinoma, neuroblastoma, pulmonary small cell carcinoma, breast cancer, colon cancer, ovary cancer, bladder cancer, etc.

The antitumor activity of the compounds can be assayed as follows.

(1) Assay of antitumor activity 0.1 ml ($10^6$ cells/mouse) portions of mouse leukemia P388 cells were implanted intraperitoneally into 7-week-old CDF1 mice. A compound was intraperitoneally administered thereinto on the first day (the day after implantation) and the fifth day after implantation, and the life or death of the mice was observed for 60 days. From the results were calculated increases in life span (ILS, %) according to the following equation. In the following equation, T means median survival days of the chemical administration group, and C means median survival days of the control group.

$$ILS = \frac{T-C}{C} \times 100$$

The results are shown in the following Table. Antitumor activity is shown as the relative ratio in the case where the ILS of dolastatin 10 is supposed to be 100.

| Example No. of compound | Antitumor activity |
| --- | --- |
| 8 | 190 |
| 12 | 190 |
| 14 | 190 |
| dolastatin 10 | 100 |

The compound of the invention, when used as a drug, can be used by formulating them into any dosage form of solid forms (e.g., tablets, hard capsules, soft capsules, granules, powders, fine granules, pills, troches, etc.), semi-solid forms (e.g., suppositories, ointments, etc.) and liquid forms (e.g., injections, emulsions, suspensions, lotions, sprays, etc.). As nontoxic additives usable in the above formulations, there can, for example, be mentioned starches, gelatin, glucose, lactose, fructose, maltose, magnesium carbonate, talc, magnesium stearate, methylcellulose, carboxymethylcellulose or salts thereof, gum arabic, polyethylene glycol, p-hydroxybenzoic acid alkyl esters, syrups, ethanol, propylene glycol, vaseline, carbowax, glycerol, sodium chloride, sodium sulfite, sodium phosphate, citric acid, etc. The drug can also contain another therapeutically effective drug.

The content of the compound of the invention in the drug varies depending on the dosage form, but it is generally preferred that the drug contains the compound at a concentration of 0.1 to 50 wt % in the case of solid and semi-solid forms, and at a concentration of 0.05 to 10 wt % in the case of liquid form.

The dose of the compound of the invention can widely be varied depending on the kind of warm-blooded animals including human beings as a subject, administration routes, the seriousness of symptoms, the diagnoses of doctors, etc., but can generally be on the order of 0.01 to 50 mg/kg per day. However, it is of course possible to administer the compound in an amount smaller than the lower limit of the above range or in an amount larger than the upper limit thereof in accordance with the seriousness of symptom of the patient and the diagnosis of the doctor as mentioned above. The above dose can be administered once a day or in divided several portions per day.

EXAMPLES

The invention is further described below according to Referential Examples and Examples.

As for the structure of compounds corresponding ing to compound numbers used in Referential Examples and Examples, please refer to the following Flow Sheets 1 and 2. Therein, Bu$^t$ represents a tert-butyl group, Boc a tert-butoxycarbonyl group, Bzl a benzyl group, Me a methyl group, B a phenyl group substituted with a halogen atom, hydroxyl group, lower alkyl group or lower alkoxy group, or a heteroaryl group, and A —CONH—R$^1$, —CSNH—R$^1$, a hydroxymethyl group, a lower alkoxycarbonyl group or a carboxyl group, wherein R$^1$ represents a lower alkyl group or a heteroaryl group.

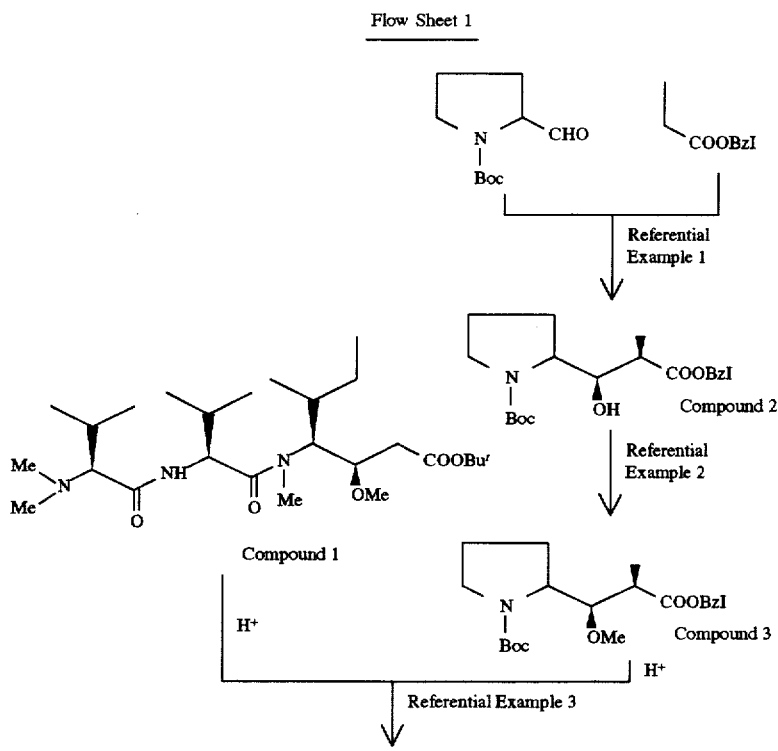

Flow Sheet 1

-continued
Flow Sheet 1
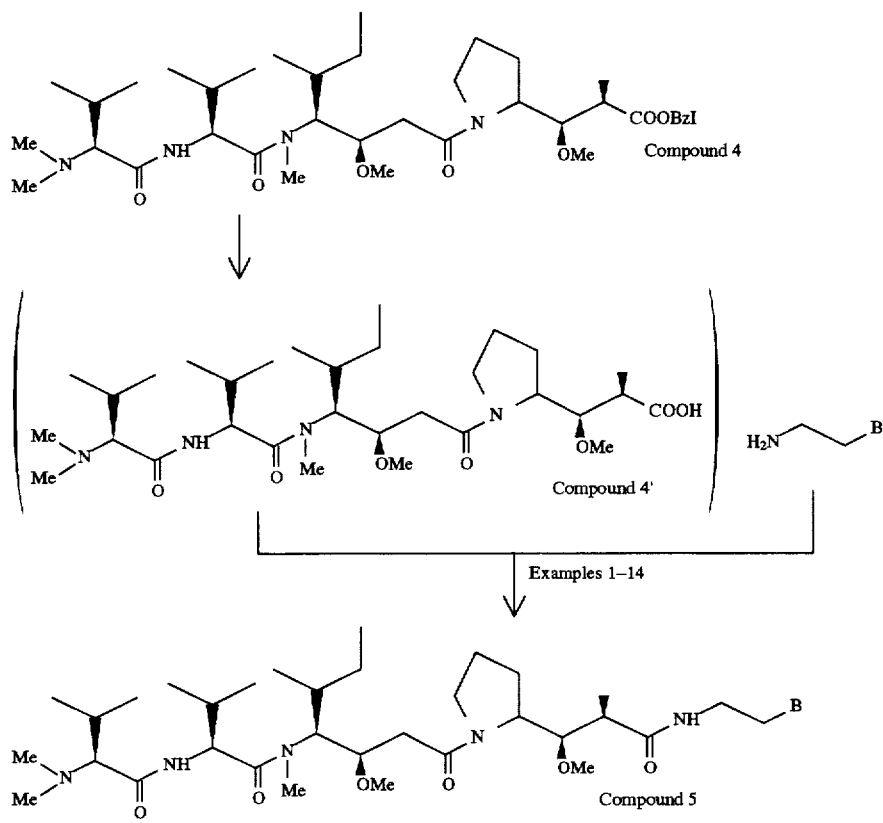
Flow Sheet 2
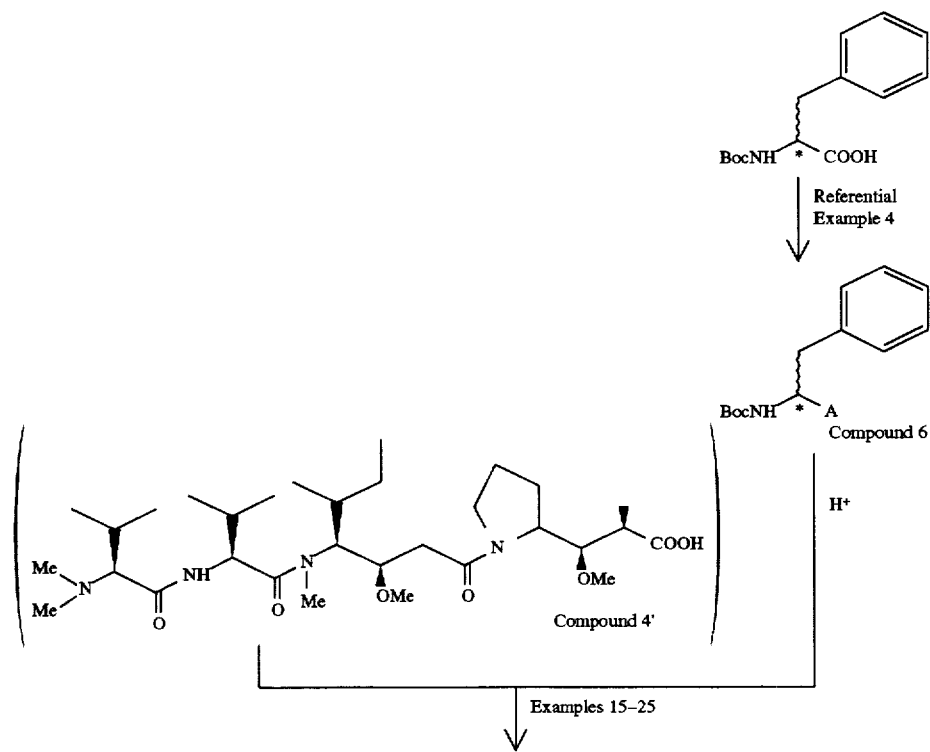

-continued
Flow Sheet 2

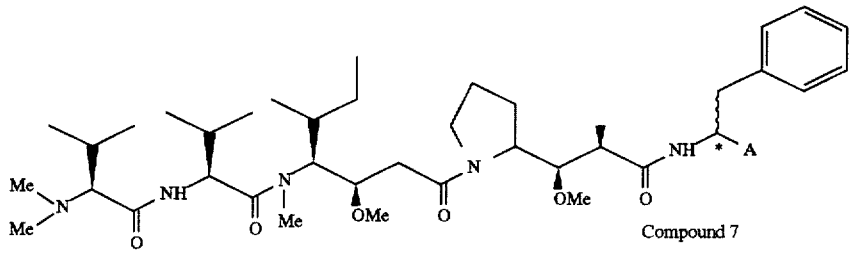

Compound 7

Referential Example 1
Preparation of compound 2

30 ml of a tetrahydrofuran-n-hexane (1:1) solution of 23.8% lithium diisopropylamide (LDA, 66.4 mmoles) is gradually poured into 40 ml of anhydrous tetrahydrofuran under stirring at -20° in an atmosphere of nitrogen, the mixture is cooled to -78°, and 9.84 g (60 mmoles) of benzyl propionate is added dropwise over a period of 30 minutes. 5 minutes later, a solution of 7.96 g (40 mmoles) of Boc-prolinal in 40 ml of tetrahydrofuran is added dropwise at the same temperature over a period of 1 hour. The mixture is stirred at the same temperature for 15 minutes, 150 ml of ice-cooled 1N-hydrochloric acid is added, and the mixture is warmed to room temperature. The mixture is extracted with ethyl acetate, the ethyl acetate layer is washed with water and dried, the solvent is distilled off under reduced pressure, and the remaining oily matter is purified by silica gel flash chromatography using ethyl acetate-n-hexane (1:5) as an eluent to obtain the desired compound 2 as colorless oily matter. 3.86 g (26.6%).

$[\alpha]_D^{27}$ -28.4°(c =0.82, MeOH); $^1$H-NMR(CDCl$_3$, δ) 1.30 (3H, d, J=7.0 Hz), 1.45 (9H, s), 1.6–2.1(m), 2.61(1H, quintet, J=7.0 Hz), 3.0–3.6(m), 3.7–4.1(m), 5.13(2H, s), 7.34(5H, s)

Referential Example 2
Preparation of compound 3

730 mg (2.01 mmoles) of compound 2 obtained in Referential Example 1 is dissolved in 10 ml of dimethylformamide, 0.7 ml (11.22 mmoles) of methyl iodide is pourd therein under stirring, and 0.16 g (4.00 mmoles) of sodium hydride (60% in mineral oil) is added therein. Stirring is continued at 0° for 1 hour, ice water is added, and the mixture is extracted with ethyl acetate-benzene (4:1). The organic layer is washed with 5% potassium hydrogen sulfate, saturated aqueous sodium bicarbonate, 5% sodium thiosulfate and saturated saline in this order, and dried. The resultant crude product is purified by silica gel flash chromatography using ethyl acetate-n-hexane (1:10) as an eluent to obtain the desired compound 3 as colorless oily matter. 530 mg (72.5%).

$[\alpha]_D^{27}$ -25.7°(c=0.389, MeOH) $^1$H-NMR(CDCl$_3$, δ)1.26 (3H, d, J=6.8 Hz), 1.45 (9H, s), 1.65–2.1(m), 2.56(1H, quintet, J=7.0 Hz), 3.0–4.0(m), 3.38(3H, s), 5.14(2H, s), 7.34(5H, s)

Referential Example 3
Preparation of compound 4

(a) 1 ml of concentrated hydrochloric acid is added to 97.1 mg (0.2 mmole) of compound 1 (known compound) under ice cooling, and the mixture is stirred at 0° for 1 hour and evaporated to dryness under reduced pressure. The residue is dissolved in 2 ml of dimethylformamide, 0.15 ml of triethylamine is added dropwise at 0° , and the mixture is again evaporated to dryness under reduced pressure.

(b) On the other hand, 76 mg (0.2 mmole) of compound 3 obtained in Referential Example 2 is dissolved in 0.5 ml of ethyl acetate, 2.0 ml of 2N-hydrogen chloride/ethyl acetate is added under ice cooling, and the mixture is brought to room temperature, stirred for 1.5 hours, evaporated to dryness under reduced pressure and then dried.

The products obtained in (a) and (b) are combined and dissolved in 0.8 ml of dimethylformamide, 34.3 mg (1.1 equivalents) of DEPC is added, the mixture is ice-cooled, 56 μl (2 equivalents) of triethylamine is added, and stirring is continued under ice cooling for 1 hour and then at room temperature overnight. The solvent is evaporated under reduced pressure, the residue is dissolved in dichloromethane, and the solution is washed with saturated aqueous sodium bicarbonate and saturated saline and dried. The resultant crude product is purified by silica gel flash chromatography using dichloromethane-methanol (20:1) as an eluent, and then by Sephadex LH-20 chromatography using n-hexane-dichloromethane-methanol (2:7.5:2.5) as an eluent to obtain the desired compound 4 as an amorphous solid. 117 mg (85.0%).

$[\alpha]_D^{26}$ -44.0°(c=0.80, MeOH) $^1$H-NMR(CDCl$_3$δ)0.7–1.5 (m), 1.27(3H, d, J=7.0 Hz), 1.5–2.25(m), 2.25–2.9(m), 3.01 (3H, s), 3.29 (3H, s), 3.35(3H, s), 3.8–4.3(m), 4.5–5.0(m), 5.13 (2H, s), 7.34(5H, s)

Referential Example 4-A
Preparation of compound 6-A
(in compound 6, A=CONH—Et, *=S)

1.33 g (5 mmoles) of Boc-phenylalanine is dissolved in 20 ml of tetrahydrofuran, and while the solution is stirred at -15°, 0.56 ml (5 mmoles) of N-methylmorpholine and then 0.67 ml (5 mmoles) of isobutyl chloroformate are added. After stirring the mixture at -15° for 5 minutes, 0.64 g (2 equivalents) of aqueous 70% ethylamine solution is added, and stirring is continued at -15° for 15 minutes and then at room temperature for 1.5 hours. The reaction solution is concentrated under reduced pressure, the residue is dissolved in ethyl acetate, the solution is washed with ice-cooled 2N-hydrochloric acid and saturated aqueous sodium bicarbonate and dried, the solvent is distilled off, and the residue is crystallized from ethyl acetate-ether-n-hexane to obtain the desired compound 6-A as needle crystals. 1.12 g (76.7%).

Melting point 123°–4°.

$^1$H-NMR(CDCl$_3$, δ)0.99(3H, t, J=7.3 Hz), 1.41 (9H, s), 2.9–3.2(m), 3.22(2H, q, J=7.3 Hz), 4.25(1H, dd, J=14.3 Hz, J=7.5 Hz), 5.04(1H, br. d)5.61(1H, br. s), 7.25(5H, s)

Referential Example 4-B
Preparation of compound 6-B
(in compound 6, A=CONH—Et, *=R)

The desired compound 6-B is obtained from BOC-D-phenylalanine in all the same manner as in Referential Example 4-A.

Referential Example 4-C
Preparation of compound 6-C
(in compound 6,

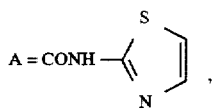

*=S)

133 mg (0.5 mmole) of Boc-phenylalanine and 50 mg (0.5 mmole) of 2-aminothiazole are dissolved in 1 ml of dimethylformamide, and while the solution is stirred at 0°, 86 mg (1 equivalent) of DEPC and 70 μl (1 equivalent) of triethylamine are added. After stirring is continued at 0° for 3 hours and then at room temperature overnight, the mixture is evaporated to dryness under reduced pressure, the residue is dissolved in dichloromethane, and the solution is washed with 10% citric acid and saturated aqueous sodium bicarbonate and dried. The crude product is purified by preparative TLC using ethyl acetate-n-hexane (3:4) as a developing solvent to obtain the desired compound 6-C as sand-like crystals. 128 mg (73.6%). Melting point 158°–160°.

$[\alpha]_D^{25}$ −11.0°(c=0.2, CHCl$_3$); $^1$H-NMR(CDCl$_3$, δ)1.41 (9H, s), 3.0–3.3 (2H, m), 4.5–4.8(1H, m), 5.0–5.2(1H, br. d), 7.23 (5H, m), 7.26(2H, dd, J=41.3 Hz, J=3.7 Hz)

Referential Example 4-D
Preparation of compound 6-D
(in compound 6,

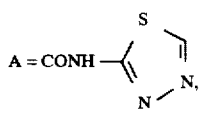

*=S)

The desired compound 6-D is obtained from BOC-phenylalanine and 2-amino-1,3,4-thiadiazole in all the same manner as in Referential Example 4-C.

$[\alpha]_D^{27}$+34.1°(c=0.960, MeOH); $^1$H-NMR(CDCl$_3$, δ)1.28 (9H, s), 3.0–3.3 (2H, m), 4.6–4.9(1H, m), 6.27(1H, d, J=7.3 Hz), 7.26 (5H, s), 8.84(1H, s), 13.5(1H, br. s)

Referential Example 4-E
Preparation of compound 6-E (in compound 6, A=CSNH—Et, *=S)

0.217 g (0.745 mmole) of compound 6-A obtained in Referential Example 4-A and 151 mg (0.5 equivalent) of Lawesson reagent are dissolved in 5 ml of benzene, and the solution is refluxed with heating for 45 minutes. The reaction solution is evaporated to dryness under reduced pressure, and the residue is purified by preparative TLC using dichloromethane-methanol (40:1) as a developing solvent to obtain the desired thioamide (compound 6-E) as a yellow waxy solid. 0.230 g (quantitative).

$^1$H-NMR(CDCl$_3$, δ)1.01(3H, t, J=7.3 Hz), 1.41 (9H, s), 3.0–3.2(2H, m), 3.3–3.7(2H, m), 4.48(1H, dd, J=14.5 Hz, J=7.9 Hz), 5.25–5.55(1H, br. d), 7.24(5H, s)

Example 1
Preparation of compound 5-A
(in compound 5,

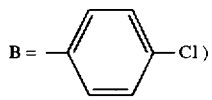

(a) 400 mg (0.58 mmole) of compound 4 obtained in Referential Example 3 is dissolved in 6 ml of t-butanol-water (9:1), 80 mg of 5% palladium-carbon is added, and the solution is stirred under a stream of hydrogen for 5 hours. The catalyst is filtered and washed, and the filtrate and the washings are evaporated to dryness under reduced pressure and dried to obtain compound 4', a carboxylic acid, as a colorless glassy solid. 337 mg (quantitative).

(b) 35 mg (60 pmoles) of the carboxylic acid obtained in (a) and 14 mg (1.5 equivalents) of p-chlorophenethylamine are dissolved in 0.5 ml of dimethylformamide, and under ice cooling and stirring, 12.4 mg (1.2 equivalents) of DEPC and 16 μl (1.88 equivalents) of triethylamine are added, and stirring is continued at 0° for at least 3 hours and then overnight allowing the ice to melt. The reaction solution is concentrated under reduced pressure, the residue is dissolved in dichloromethane, and the solution is washed with saturated aqueous sodium bicarbonate and saturated saline and dried. The resultant crude product is purified by preparative TLC using dichloromethane-methanol (10:1) as a developing solvent and then Sephadex LH-20 chromatography using n-hexane-dichloromethane-methanol (2:7.5:2.5) as an eluent to obtain the desired compound 5-A as amorphous powder. 35.2 mg (79.6%).

$[\alpha]_D^{28}$ −32.9°(c=0.292, MeOH); $^1$H-NMR(CDCl$_3$, δ)0.7–1.1(m), 1.22(3H, d, J=7.0 Hz), 2.26(6H, s), 3.03(3H, s), 3.31(3H, s), 3.36 (3H, s), 3.7–4.2(m), 4.79(1H, dd, J=9.2 Hz, 6.6 Hz), 6.86(1H, br. d), 7.1–7.3(4H, m)

Examples 2 to 15

The following compounds are obtained by reacting compound 4' with the corresponding phenethylamine derivative in the same manner as in Example 1.

| Example | Compound | B | [α] D (MeOH) | $^1$H-NMR(CDCl$_3$, δ) |
|---|---|---|---|---|
| 2 | 5-B | ⟨benzene ring⟩-F | −39.3° (C=0.293) (28°) | 0.7~1.1(m), 1.21(3H, d, J=7.0Hz), 1.5~2.2(m), 2.2~2.65(m), 3.02(3H, s), 3.31(3H, s), 3.36(3H, s), 3.7~4.25(m), 4.76(1H, dd, J=8.6Hz, J=6.7Hz), 6.9~7.3(4H, m) |

-continued

| Example | Compound | B | [α] D (MeOH) | ¹H-NMR(CDCl₃, δ) |
|---|---|---|---|---|
| 3 | 5-C | (phenyl)-OH (para) | −31.3° (C=0.364) (27°) | 0.65~1.3(m), 1.21(3H, d, J=7.3Hz), 1.5~2.3(m), 2.52(6H, s), 3.05(3H, s), 3.30(3H, s), 3.34(3H, s), 3.7~4.2(m), 4.5~4.8(m), 6.89(4H, dd, J=24.4Hz, J=8.6Hz) |
| 4 | 5-D | (phenyl)-OMe (para) | −23.7° (C=0.351) (27°) | 0.7~1.15(m), 1.21(3H, d, J=7.0Hz), 2.90(6H, s), 3.01(3H, s), 3.31(3H, s), 3.36(3H, s), 3.78(3H, s), 4.5~4.85(m), 6.97(4H, dd, J=27.9Hz, J=8.8Hz) |
| 5 | 5-E | (phenyl)-F (meta) | −38.0° (C=0.277) (28°) | 0.65~1.2(m), 1.22(3H, d, J=7.3Hz), 1.5~2.3(m), 2.55(6H, br. s), 3.02(3H, s), 3.31(3H, s), 3.36(3H, s), 3.7~4.25(m), 4.75(1H, dd, J=8.6Hz, J=6.8Hz) 6.7~7.3(4H, m) |
| 6 | 5-F | (phenyl)-Cl (meta) | −31.2° (C=0.284) (28°) | 0.7~1.2(m), 1.22(3H, d, J=7.1Hz), 1.5~2.3(m), 2.5~2.9(m), 3.02(3H, s), 3.31(3H, s), 3.36(3H, s), 3.7~4.25(m), 4.5~4.9(m), 7.18(4H, s) |
| 7 | 5-G | (phenyl)-OH (meta) | −30.3° (C=0.307) (25°) | 0.7~1.1(m), 1.19(3H, d, J=7.3Hz), 1.5~2.2(m), 2.39(6H, s), 2.65~2.9(m), 3.08(3H, s), 3.33(3H, s), 3.37(3H, s), 3.6~4.25(m), 4.6~5.05(m), 5.9~6.2(m), 6.55~7.2(5H, m) |
| 8 | 5-H | (phenyl)-F (ortho) | −44.6° (C=0.435) (23°) | 0.65~1.2(m), 1.21(3H, d, J=7.0Hz), 1.5~2.3(m), 2.5(6H, br. s), 3.01(3H, s), 3.31(3H, s), 3.36(3H, s), 4.0~4.3(m), 4.76(1H, dd, J=8.6Hz, J=6.4Hz), 6.9~7.3(4H, m) |
| 9 | 5-I | (phenyl)-Cl (ortho) | −44.5° (C=0.339) (22°) | 0.7~1.2(m), 1.22(3H, d, J=6.8Hz), 1.5~2.2(m), 2.3~2.7(m), 3.01(3H, s), 3.31(3H, s), 3.37(3H, s), 3.75~3.95(m), 4.0~4.25(m), 4.77(1H, dd, J=8.8Hz, J=6.6Hz), 7.0~7.4(4H, m) |
| 10 | 5-J | (phenyl)-I (ortho) | −35.2° (C=0.328) (28°) | 0.7~1.2(m), 1.23(3H, d, J=7.3Hz), 1.4~2.25(m), 2.63(6H, br. s), 3.01(3H, s), 3.31(3H, s), 3.37(3H, s), 3.75~3.95(m), 3.95~4.3(m), 4.5~4.9(m), 7.0~7.4(4H, m) |
| 11 | 5-K | (phenyl)-CH3 (ortho) | −33.7° (C=0.348) (26°) | 0.65~1.1(m), 1.23(3H, d, J=6.8Hz), 1.5~2.2(m), 2.34(3H, s), 2.92(6H, s), 3.00(3H, s), 3.31(3H, s), 3.37(3H, s), 3.95~4.3(m), 4.5~4.85(m), 7.13(4H, s) |
| 12 | 5-L | (phenyl)-HO (ortho) | −35.0° (C=0.345) (25°) | 0.7~1.2(m), 1.24(3H, d, J=7.0Hz), 1.5~2.3(m), 2.47(6H, br. s), 3.06(3H, s), 3.33(3H, s), 3.34(3H, s), 3.9~4.3(m), 4.77(1H, dd, J=8.8Hz, J=6.7Hz), 6.65~7.2(4H, m) |

-continued

| Example | Compound | B | [α] D (MeOH) | $^1$H-NMR(CDCl$_3$, δ) |
|---|---|---|---|---|
| 13 | 5-M | MeO-phenyl | −37.5° (C=0.311) (28°) | 0.65−1.1(m), 1.20(3H, d, J=7.0Hz), 1.5−2.25(m), 2.48(6H, br. s), 3.01(3H, s), 3.31(3H, s), 3.35(3H, s), 3.83(3H, s), 3.95−4.25(m), 4.76(1H, dd, J=8.4Hz, J=6.6Hz), 6.7−7.3(4H, m) |
| 14 | 5-N | thiophene | n.d. | 0.6−1.15(m), 1.24(3H, d, J=6.8Hz), 1.5−2.2(m), 2.30(6H, s), 3.02(3H, s), 3.32(3H, s), 3.37(3H, s), 4.0−4.3(m), 4.79(1H, dd, J=9.0Hz, J=6.7Hz), 6.7−7.2(3H, m) |
| 15 | 5-O | pyridine | −41.2° (C=1.68) (25°) | 0.7−1.1(m), 1.21(3H, d, J=7.3Hz), 1.5−2.3(m), 2.54(6H, br. s), 3.01(3H, s), 3.31(3H, s), 3.36(3H, s), 3.5−3.95(m), 4.0−4.3(m), 4.75(1H, dd, J=9.2Hz, J=6.4Hz), 7.0−7.75(4H, m) |

Example 16

Preparation of compound 7-A
(in compound 7,

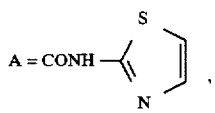

*=S)

70 mg (0.2 mmole) of compound 6-C obtained in Referential Example 4-C is dissolved in 1 ml of 50% trifluoroacetic acid-dichloromethane at 0°, and the solution is brought to room temperature, stirred for 3 hours and evaporated under reduced pressure. The residue is washed thoroughly with ether and dried under reduced pressure.

The above compound and 88 mg (0.15 mmole) of compound 4' obtained in (a) of Example 1 are dissolved in 1.5 ml of dimethylformamide, and under ice cooling and stirring, 30 mg (0.184 mmole) of DEPC and 41 mg (0.406 mmole) of triethylamine are added. Stirring is continued at 0° for 3 hours and then at room temperature overnight, the reaction solution is evaporated under reduced pressure, the residue is dissolved in dichloromethane, and the solution is washed with saturated aqueous sodium bicarbonate and saturated saline and dried. The resultant product is purified by preparative TLC using dichloromethane-methanol (10:1) as a developing solvent to obtain the desired compound 7-A as white powder. 86.5 mg (69.6%).

$[α]_D^{28}$ −26.1°(c=0.3185, MeOH); $^1$H-NMR(CDCl$_3$, δ)0.7−1.3(m), 1.11(3H, d, J=6.6 Hz), 2.98(3H, s), 2.99(3H, s), 3.34(6H, s), 3.5−4.2(m), 4.5−5.1(m), 7.23(5H, s), 7.41 (2H, dd, J=56.5 Hz, J=4.0 Hz)

Examples 17 to 24

Compounds 6-A, 6-B, 6-D and 6-E obtained in Referential Examples 4-A, 4-B, 4-D and 4-E are deprotected respectively according to Example 16, and then reacted with compound 4' to obtain the desired compounds 7-B, 7-C, 7-D and 7-E. Likewise, by reaction of L- or D-phenylalanine methyl ester hydrochloride or phenylalanine ethyl ester or phenylalaninol with compound 4', the corresponding compounds 7-F, 7-G, 7-H and 7-I are obtained. The results are shown in the following Table.

| Example | Compound | A | * | [α] D (MeOH) | $^1$H-NMR(CDCl$_3$, δ) |
|---|---|---|---|---|---|
| 17 | 7-B | —CONH—Et | S | −51.2° (C=0.3475) (27°). | 0.6−1.2(m), 1.5−2.0(m), 2.42(6H, s), 3.02(3H, s), 3.31(3H, s), 3.35(3H, s), 3.6−4.2(m), 4.5−4.9(m) 7.25(5H, s) |
| 18 | 7-C | —CONH—Et | R | −50.8° (C=0.323) (27°) | 0.6−1.1(m), 1.1−1.4(m), 1.5−2.5(m), 2.96(3H, s), 3.24(3H, s), 3.33(3H, s), 3.6−4.2(m), 4.5−4.9(m), 7.23(5H, s) |
| 19 | 7-D | —CONH—(thiadiazole) | S | −30.6° (C=0.310) (23°) | 0.7−1.2(m), 1.5−2.2(m), 2.36(6H, br. s), 3.10(3H, s), 3.34(3H, s), 3.36(3H, s), 4.5−5.1(m), 5.90(1H, br. d), 7.25(5H, s), 8.82(1H, s) |

-continued

| Example | Compound | A | * | [α] D (MeOH) | 1H-NMR(CDCl3, δ) |
|---|---|---|---|---|---|
| 20 | 7-E | —CSNH—Et | S | −47.8° (C=0.347) (22°) | 0.6~1.2(m), 1.5~2.2(m), 2.34(6H, s), 3.08(3H, s), 3.31(3H, s), 3.37(3H, s), 3.8~4.2(m), 4.5~5.1(m), 7.25(5H, s) |
| 21 | 7-F | —COOMe | S | n.d. | n.d. |
| 22 | 7-G | —COOMe | R | −48.7° (C=0.3285) (28°) | 0.7~1.2(m), 1.21(3H, d, J=7.3Hz), 1.5~2.3(m), 2.50(6H, br. s), 3.02(3H, s), 3.32(3H, s), 3.34(3H, s), 3.70(3H, s), 3.8~4.3(m), 4.5~5.0(m), 7.0~7.4(5H, m), |
| 23 | 7-H | —COOEt | S | −56.4° (C=0.3265) (27°) | 0.7~1.1(m), 1.21(3H, t, J=7.3Hz) 2.70(6H, br. s), 3.02(3H, s), 3.32(3H, s), 3.34(3H, s), 4.15(2H, q, J=7.3Hz), 4.5~4.9(m), 7.24(5H, s), |
| 24 | 7-I | —CH2OH | S | −51.6° (C=0.2735) (27°) | 0.6~1.2(m), 1.13(3H, d, J=7.0Hz), 1.5~2.3(m), 2.44(6H, br. s), 3.02(3H, s), 3.32(3H, s), 3.40(3H, s), 3.9~4.4(m), 4.76(1H, dd, J=8.8Hz, J=6.8Hz), 7.25(5H, s) |

Example 25

Preparation of compound 7-J (in compound 7, A=COOH, *=S)

38.1 mg (50 μmoles) of compound 7-F obtained in Example 21 is dissolved in 0.5 ml of methanol, 55 μl (55 μmoles) of 1N-sodium hydroxide is added, and the mixture is stirred at room temperature for 3 hours. The mixture is ice-cooled, 55 μl of 1N-hydrochloric acid is added, the mixture is evaporated to dryness under reduced pressure, and the tetrahydrofuran-soluble part of the residue is purified by Sephadex LH-20 chromatography using n-hexane-dichloromethane-methanol (2:7.5:2.5) as an eluent to obtain powder of the desired compound 7-J. 37.4 mg (100%).

$[α]_D^{30}$ −33.4°(c=0.3265, MeOH); 1H-NMR(CDCl3, δ)0.6–1.3(m), 1.5–2.2(m), 2.6–2.8(6H, m), 3.07(3H, s), 3.33 (3H, s), 3.38 (3H, s), 3.6–4.2(m), 4.5–4.9(m), 7.21(5H, s)

Example 26

Preparation of compound 7-K (in compound 7, A=COOH, *=R)

Compound 7-K is obtained from compound 7-G in all th-e same manner as in Example 25.

$[α]_D^{29}$ −4 63.4°(c=0.330, MeOH); 1H-NMR(CDCl3, δ)0.7–1.4(m), 1.5–2.3(m), 2.71(6H, br. s), 3.04(3H, s), 3.32 (3H, s), 3.37 (3H, s), 4.6–5.0(m), 7.22(5H, s)

We claim:

1. A peptide derivative of the formula:

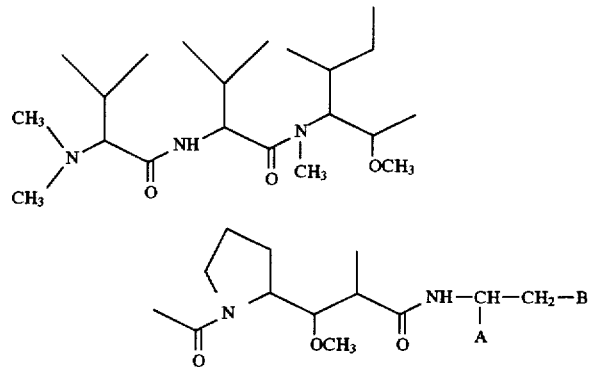

wherein A represents a hydrogen atom, and B represents a heteroaryl group selected from the group consisting of thienyl, furyl, pyrrolyl, imidazolyl, thiazolyl, oxazolyl, thiadiazolyl, tetrazolyl, pyridyl, pyrimidinyl and triazinyl, or a salt thereof.

2. The peptide derivative or salt thereof according to claim 1, wherein B represents a thienyl group or a pyridyl group.

* * * * *